United States Patent
Wang et al.

(10) Patent No.: US 6,956,048 B2
(45) Date of Patent: Oct. 18, 2005

(54) PHARMACEUTICAL EMULSIONS FOR RETROVIRAL PROTEASE INHIBITORS

(75) Inventors: Youmin Wang, Brookfield, WI (US); Walter Morozowich, Kalamazoo, MI (US)

(73) Assignee: Pharmacia & UpJohn Company, Kalamazoo, MI (US)

(*) Notice: Subject to any disclaimer, the term of this patent is extended or adjusted under 35 U.S.C. 154(b) by 289 days.

(21) Appl. No.: 09/532,396

(22) Filed: Mar. 22, 2000

(65) Prior Publication Data
US 2003/0068338 A1 Apr. 10, 2003

Related U.S. Application Data
(60) Provisional application No. 60/127,026, filed on Mar. 31, 1999.

(51) Int. Cl.⁷ .......................... A61K 31/44; A01N 43/40
(52) U.S. Cl. ....................... 514/336; 424/450
(58) Field of Search ........................... 514/336; 424/450

(56) References Cited

U.S. PATENT DOCUMENTS

| | | | | |
|---|---|---|---|---|
| 5,616,342 | A | * | 4/1997 | Lyons |
| 5,665,700 | A | | 9/1997 | Cho et al. |
| 5,693,337 | A | * | 12/1997 | Suzuki et al. |
| 5,852,195 | A | * | 12/1998 | Romines et al. |
| 5,952,383 | A | | 9/1999 | Metziger et al. |

FOREIGN PATENT DOCUMENTS

| | | | | |
|---|---|---|---|---|
| GB | 2 257 359 A | 1/1993 | .......... | A61K/37/02 |
| WO | WO91/14429 | 10/1991 | .......... | A61K/31/35 |
| WO | WO96/39142 | 12/1996 | .......... | A61K/31/47 |
| WO | WO98/22106 | 5/1998 | .......... | A61K/31/425 |
| WO | WO98/37869 | 9/1998 | .......... | A61K/9/107 |
| WO | WO 99 06043 A | 2/1999 | | |
| WO | WO99/06043 | 2/1999 | .......... | A61K/31/44 |
| WO | WO 99 06044 A | 2/1999 | | |
| WO | WO99/06044 | 2/1999 | .......... | A61K/31/44 |

OTHER PUBLICATIONS

Remington's Pharmaceutical Sciences, 18th ed., p. 1172, 1286, 1316 and 1317.*

* cited by examiner

Primary Examiner—San-Ming Hui
(74) Attorney, Agent, or Firm—Flynn, Thiel, Boutell & Tanis, P.C.

(57) ABSTRACT

The present invention provides an emulsion formulation with high oral bioavailability containing lecithin as an emulsifier and solubilizing agent to achieve a high loading of the pyranone compound of formula I

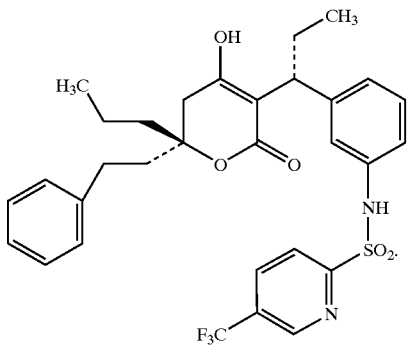

2 Claims, No Drawings

PHARMACEUTICAL EMULSIONS FOR RETROVIRAL PROTEASE INHIBITORS

CROSS REFERENCE TO RELATED APPLICATIONS

This application claims the benefit of the following provisional application: U.S. Ser. No. 60/127,026, filed Mar. 31, 1999, under 35 USC §119(e)(1).

FIELD OF THE INVENTION

The present invention relates to novel pharmaceutical compositions in the form of emulsions with high oral bioavailability and prolonged blood levels for compounds which are inhibitors of retroviral protease. In particular, the composition is a safe emulsion formulation comprising a HIV protease inhibitor, an oil component, an emulsifying agent consisting of lecithin and solvents for pediatric patients.

BACKGROUND OF THE INVENTION

It has recently been discovered that certain pyranone compounds inhibit retroviral protease and thus they are useful for treating patients infected with human immunodeficiency virus (HIV) which results in acquired immunodeficiency syndrome (AIDS). In particular, the pyranone compound of formula I has been found to be especially effective as an inhibitor of retroviral protease.

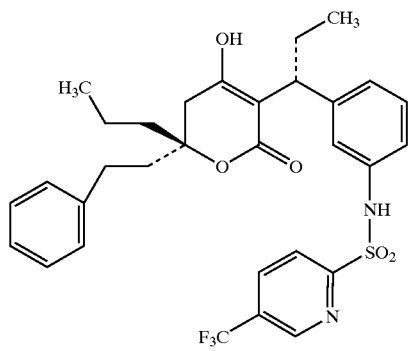

I

Several emulsion formulations of HIV drug are available in the prior art. However, these formulations require synthetic surfactants as emulsifiers to stabilize the compositions. For example, International publication WO 99/06043 discloses a self-emulsifying formulation which comprises the above pyranone compound of formula I, a mixture of diglyceride and monoglyceride, one or more solvents and one or more surfactants. Another example, WO 99/06044 discloses a discloses a self-emulsifying formulation which comprises the above pyranone compound of formula I, a basic amine, one or more solvents and one or more surfactants. Unfortunately, the catalog of suitable synthetic surfactants is limited. Although their potential scope is considerable, extensive toxicological studies are generally necessary to prove the harmlessness of the surfactants used in an emulsion formulation. Especially, the potentially adverse effect of surfactants on the newborn or small children is of major concern in today's society. Newborn and small children generally are more susceptible to chemical agents than adults.

Recognizing the potential problems, the present invention is directed toward pharmaceutical compositions in the form of emulsions which use natural or nontoxic lecithin as an emulsifier. The formulations of the present invention do not contain synthetic surfactants and, therefore, they are much safer for adult and pediatric use. It has also been discovered that lecithin dramatically increases the solubility of pyranone compound of formula I in oils. As a result, a high concentration of an emulsion formulation with high oral bioavailability can be prepared. Most surprisingly, the formulations of the present invention produce a prolonged blood level curve. Therefore, they have the potential for sustained release and high trough levels in the clinic.

INFORMATION DISCLOSURE

U.S. Pat. No. 5,852,195 discloses pyranone compounds of formula I useful to treat retroviral infections.

The International Publication No. WO 96/39142 discloses compositions which increase the bioavailability of protease inhibitors.

The International Publication No. WO 99/06043 discloses a self-emulsifying formulation which comprises the above pyranone compound of formula I, a mixture of diglyceride and monoglyceride, one or more solvents and one or more surfactants.

The International Publication No. WO 99/06044 discloses a discloses a self-emulsifying formulation which comprises the above pyranone compound of formula I, a basic amine, one or more solvents and one or more surfactants.

U.S. Pat. No. 5,693,337 discloses a lipid emulsion which comprises a drug, an oil component, an emulsifying agent containing lecithin, water and citric acid.

U.S. Pat. No. 5,665,700 discloses a pharmaceutical formulation comprising (a) a hydrophilic phase containing water, a biologically active material and lecithin; (b) a lipophilic phase containing one or more oils, a phospholipid and a lipophilic surfactant.

The International Publication No. WO 91/14429 discloses a composition for oral administration containing an active ingredient ipriflavone in combination with oily vehicles.

The International Publication No. WO 98/01118 discloses a pharmaceutical composition for oral delivery, including a liquid carrier oil, a homogenizing agent and a surfactant, an active agent and one or more excipients or carriers.

The International Publication No. WO 98/37869 discloses a O/W medical fat emulsion for oral administration which comprises an oil component, an emulsifier and a medicine as the indispensable constituents and dispersed in water.

The International Publication No. WO 98/22106 discloses a liquid pharmaceutical composition providing improved oral bioavailability for compounds which are inhibitors of HIV protease.

UK Patent application, GB2,257,359A discloses pharmaceutical compositions suitable for oral administration comprising a cyclosporin, 1,2-propylene glycol, a mixed mono-, di-, and tri-glyceride and a hydrophilic surfactant.

SUMMARY OF THE INVENTION

One object of the present invention is to provide a safe pharmaceutical composition comprising the pyranone compound of formula I for HIV infected patients.

Another object of the present invention is to provide a safe pediatric formulation for HIV infected infants or small children who are especially vulnerable to the side effects of synthetic surfactants.

A further object of the present invention is to provide an emulsion formulation containing a high drug load of the pyranone compound of formula I for convenient administration which also has high oral bioavailability.

A still further object of the present invention is to provide an emulsion formulation which is capable of producing a prolonged blood level curve indicating sustained release.

The objects of the present invention have been accomplished in that the present invention provides an emulsion formulation containing natural, nontoxic lecithin as an emulsifier while at the same time allows a high loading of the pyranone compound of formula I. This novel formulation also achieves the desired high oral bioavailability and produces a prolonged blood level curve The present invention specifically provides a pharmaceutical composition which comprises:
(a) a therapeutically effective amount of the compound of formula I,
(b) an oil component selected from the group consisting of mono-, di-, tri-glyceride or a mixture thereof wherein the monoglyceride and diglyceride are mono- and di-unsaturated fatty acid esters of glycerol having sixteen to twenty-two carbon atom chain length, wherein triglyceride is a saturated fatty acid ester of glycerol having six to twelve carbon atom chain length,
(c) an emulsifying agent consisting of lecithin, and
(d) a liquid phase comprising one or more pharmaceutically acceptable solvents.

DETAILED DESCRIPTION OF THE INVENTION

In accordance with the present invention, there is a pharmaceutical composition comprising a pyranone compound as a pharmaceutically active agent in an emulsion vehicle.

For the purpose of the present invention, the term "pyranone compound" refers to compounds of formula I as defined above and its pharmaceutically acceptable salt thereof.

The compounds of formula I inhibit retroviral protease and thus inhibit the replication of the virus. They are useful for treating patients infected with human retrovirus, such as human immunodeficiency virus (strains of HIV-1 or HIV-2) or human T-cell leukemia viruses (HTLV-I or HTLV-II) which results in acquired immunodeficiency syndrome (AIDS) and/or related diseases. The compound of formula I is disclosed and claimed in U.S. Pat. No. 5,852,195, incorporated herein by reference, and can be prepared according to the procedures described in said U.S. Patent.

The amount of active ingredient in the emulsion formulations of the present invention may vary or be adjusted widely depending on the intended route of administration, ages of patients being treated, the severity of the retroviral infection and the required concentration.

In preparing the emulsion formulations of the present invention, the amount of active ingredient is not particularly restricted up to 200 mg/ml (20% by weight) for maintaining high oral bioavailability, but preferably ranges from about 1% to about 20%, and more preferably from about 2% to about 15%, by weight of the total composition.

The emulsion formulations of the present invention may be administered orally, or parenterally at a dosage to obtain and maintain a concentration, that is, an amount, or blood-level of the active ingredient in the patients, which will be therapeutically effective. Generally, such therapeutically effective amount of active ingredient ranges from about 0.1 to about 300 mg/kg of body weight per day. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two or more times per day.

The term "oil component" refers to monoglyceride, diglyceride, triglyceride, or a mixture comprising at lest two members of these three glycerides.

Preferably, the oil component is triglyceride, a mixture of diglyceride and monoglyceride in a ratio of from about 9:1 to about 1:9 by weight, a mixture of diglyceride and triglyceride in a ratio of from about 9:1 to about 1:9 by weight, or a mixture of monoglyceride, diglyceride and triglyceride in a ratio of from about 1 to about 8 parts of diglyceride per 10 parts of the mixture, about 1 to 5 parts of monoglyceride per 10 parts of the mixture, and about 1 to about 8 parts of triglyceride per 10 parts of the mixture.

More preferably, the oil component is triglyceride, a mixture of diglyceride and monoglyceride in a ratio of about 8:2 (diglyceride:monoglyceride) by weight, a mixture of diglyceride and triglyceride in a ratio of about 2:8 (triglyceride:diglyceride) by weight.

Diglyceride (hereinafter DGO) of the present invention refers to a long chain fatty acid ester of glycerol having structural formula $HOCH_2$—$CH(O_2CR)$—$CH_2(O_2CR)$ or $(RCO_2)CH_2$—$CH(OH)$—$CH_2(O_2CR)$, wherein R is mono-unsaturated or di-unsaturated alkyl group having fifteen to twenty-one carbon atoms. The preferred diglyceride is diolein (R is mono-unsaturated alkyl group with seventeen carbon atoms), dilinoleate (R is di-unsaturated alkyl group with seventeen carbon atoms), or a mixture of diolein and dilinoleate. The most preferred diglyceride is diolein.

Monoglyceride (hereinafter GMO) of the present invention refers to a long chain fatty acid ester of glycerol having structural formula $HOCH_2$—$CH(OH)$—$CH_2(O_2CR)$ or $HOCH_2$—$CH(O_2CR)$—$CH_2OH$, wherein R is a mono-unsaturated or di-unsaturated alkyl group having fifteen to twenty-one carbon atoms. The preferred monoglyceride is monoolein (R is mono-unsaturated alkyl group with seventeen carbon atoms), monolinoleate (R is di-unsaturated alkyl group with seventeen carbon atoms), or a mixture of monoolein and monolinoleate. The most preferred monoglyceride is monoolein.

Triglyceride (hereinafter MCT) of the present invention refers to a medium chain fatty acid ester of glycerol having structural formula $R^1OCH_2$—$CH(O_2CR^1)$—$CH_2(O_2CR^1)$, wherein $R^1$ is a saturated alkyl group having five to eleven carbon atoms. The preferred triglyceride is under brand names Miglyol 810, Miglyol 812, Miglyol 829, etc. which refer to different grades of fractionated and purified coconut oil consisting mainly of medium chain triglycerides.

In preparing the emulsion of the present invention, the amount of the oil component is not particularly restricted, but preferably ranges from about 5% to about 40%, more preferably from about 10% to about 30%, and most preferably from about 10% to about 20%, by weight of the total composition.

An oil component which comprises the mixture of diglyceride, monoglyceride or triglyceride may be prepared by mixing individual oil in appropriate proportion or by partial hydrolysis of triglyceride, or transesterification reaction of triglycerides or diglycerides with glycerol.

All of the glycerides of the present invention are known and can be obtained by conventional methods from a broad spectrum of water-immiscible material, such as soybean oil, avocado oil, squalene oil, sesame oil, olive oil, canola oil, corn oil, rapeseed oil, safflower oil, sunflower oil, coconut oil or mixtures thereof.

The term "lecithin" used herein refers monoaminomonophospholipid, a group of substances having structure formula FACOO—$CH_2$—CH(OOCFA)—$CH_2$—$OPO_4$—$NR'_3$, wherein FA is a fatty acid, R' is an alkyl radical. Lecithin also refers to esters of oleic, steric, palmitic, or other fatty acids with glycerolphosphoric acid and choline. Lecithin may be, for instance, yolk lecithin and soybean lecithin, or synthetic nontoxic didecanoyl phosphatidycholine, dilauroyl phosphatidycholine, dimyristoyl phosphatidycholine, dipalmitoyl phosphatidycholine or a mixture thereof. Therefore, lecithin is not restricted to specific ones so far as they have compositions comprising the foregoing element. Lecithin is used as a emulsifying agent in the present invention. It also operates as a solubilizing agent.

In preparing the lipid emulsion of the present invention, the amount of lecithin to be used is not particularly restricted, but preferably ranges from about 0.5% to about 20%, more preferably from about 1% to about 10% and most preferably from about 2% to about 5%, by weight of the total composition.

Solvents of the present invention refer to propylene glycol, polyethylene glycol, glycerol, triacetin, dimethyl isosorbide, glycofurol, propylene carbonate, ethanol, water, dimethyl acetamide or a mixture thereof. The preferred solvent is propylene glycol, ethanol, water or a mixture thereof. The most preferred solvent is water.

The term "q.s." used herein refers to quantum sufficit or as much as being sufficient.

In the preparation of the lipid emulsion of the present invention, the amount of solvent(s) is not particularly restricted, but preferably ranges from about 20% to 95% by weight of the total composition.

If desired, the compositions of the present invention may further comprise conventional pharmaceutical additives such as coloring agents, flavoring agents, thickening agents, stabilizers such as sodium deoxycholate, anti-oxidants such as BHT or vitamin E, and preserving agents such as methyl paraben, or propyl paraben.

The compositions of the present invention may be prepared in a conventional manner, for example, (1) preparing an oil phase by dissolving an active ingredient in a mixture of an oil component, solvent(s), lecithin and optional water-immiscible excipients by heat, (2) preparing an aqueous phase by dissolving optional excipients in water, (3) combining the oil phase and the aqueous phase using a high energy homogenizer to achieve a submicron lipid emulsion.

The pharmaceutical compositions of the present invention will be better understood in connection with the following examples, which are intended as an illustration of and not a limitation upon the scope of the invention. Without further elaboration, it is believed that one skilled in the art can, using the preceding description and the information provided in the examples below, practice the present invention to its fullest extent.

EXAMPLE 1

| Component | Weight (mg) |
| --- | --- |
| Compound of Formula I | 60 |
| Miglyol 812 | 200 |
| Propylene Glycol | 100 |
| Lecithin | 20 |
| Na Deoxycholate | 0.5 |
| glycerine | 24 |
| Methyl paraben | 1.8 |
| Propyl paraben | 0.2 |
| Water | q.s. |

EXAMPLE 2

| Component | Weight (mg) |
| --- | --- |
| Compound of Formula I | 60 |
| GDO/GMO (8:2) | 200 |
| Propylene Glycol | 100 |
| Lecithin | 20 |
| Na Deoxycholate | 0.5 |
| glycerine | 2.4 |
| Methyl paraben | 1.8 |
| Propyl paraben | 0.2 |
| Water | q.s. |

EXAMPLE 3

| Component | Weight (mg) |
| --- | --- |
| Compound of Formula I | 60 |
| Miglyol 812 | 200 |
| Propylene Glycol | 100 |
| Lecithin | 20 |
| Na Deoxycholate | 0.5 |
| glycerine | 24 |
| Methyl paraben | 1.8 |
| Propyl paraben | 0.2 |
| Water | q.s. |

The examples 1 and 3 are the same formulation but different particle sizes

EXAMPLE 4

| Component | Weight (mg) |
| --- | --- |
| Compound of Formula I | 60 |
| GDO | 200 |
| Propylene Glycol | 100 |
| Lecithin | 20 |
| Na Deoxycholate | 0.5 |
| glycerine | 2.4 |
| Methyl paraben | 1.8 |
| Propyl paraben | 0.2 |
| Water | q.s. |

EXAMPLE 5

| Component | Weight (mg) |
| --- | --- |
| Compound of Formula I | 60 |
| MCT/GDO (8:2) | 200 |
| Lecithin | 20 |
| BHT | 0.1 |

-continued

| Component | Weight (mg) |
|---|---|
| glycerine | 2.4 |
| Water | q.s. |

Oral Bioavailability Test (i) Sprague-Dawley male rats were selected for the in vivo oral bioavailability study. Each rat was prepared by the surgical implantation of an indwelling cannula in the superior vena cava. Each rat, in the weight range of 300–400 g, was fasted overnight prior to dosing. Each formulation was orally administered to a group of rats (n=6) at a 20 mg/kg dose. The formulations with high concentration of the compound of formula I (typically 50 mg/g) was diluted by 25-fold with water and injected directly into the rat's stomach using oral gavage. Serial blood samples of 0.25 ml were obtained from the indwelling cannula at 0.25, 0.5, 1, 2, 4, 6, 8, 12, and 24 hours after dosing. These blood samples were analyzed using a HPLC assay specific for the compound of formula I. Drug concentrations in the blood of the test rats are plotted against the time after the drug is administered through an intravenous (i.v.) or oral route and the AUCs (the Area Under the Pasma Concentration-Time Curve) are integrated using the trapezoidal rule to calculate the absolute bioavailability as shown in Table 1.

$$\text{Absolute bioavailability}(F) = \frac{(AUC)_{oral}/Dose_{oral}}{(AUC)_{iv}/Dose_{iv}}$$

(ii) Male Beagle dogs were also selected for the in vivo oral bioavailability study. Each dog, in the weight range of 13.5–17.5 kg, was fasted overnight and a light snack was given 30 minutes prior to dosing. Dogs were fed with regular dog food 4 hours after dosing. Each formulation was orally administered to a group of dogs (n=5) at a 20 mg/kg dose. The formulations of the compound of formula I (50 mg/g) were encapsulated in gelatin capsules and administered. Serial blood samples of 2 ml were obtained from the jugular vein at 20, 40 minutes and 1, 2, 4, 6, 8, 12, and 24 hours after dosing. These blood samples were analyzed using a HPLC assay specific for the compound of formula I. The blood concentrations of the compound of formula I are plotted against the time and the AUCs are obtained to calculate the absolute bioavailability. The results are shown in Table 2.

TABLE 1

Absolute Mean Oral Bioavailability in Rats

| Example No. | Absolute Mean Oral Bioavailability (%) |
|---|---|
| 1 | 36 |
| 2 | 24 |
| 3 | 40 |
| 4 | 34 |
| Aqueous suspension of free acid of the compound of formula I | <20 |

TABLE 2

Absolute Mean Oral Bioavailability in Dogs

| Example No. | Absolute Mean Oral Bioavailablity (%) |
|---|---|
| 1 | 31.4 |
| 2 | 33.0 |
| Free Acid of the compound formula I powder in Hard Gelatin Capsules | 1.5 |

We claim:

1. A submicron lipid emulsion pharmaceutical composition selected from the group consisting of a composition of Example 1 as follows:

| Component | Weight (mg) |
|---|---|
| Compound of Formula 1 | 60 |
| Triglyceride | 200 |
| Propylene Glycol | 100 |
| Lecithin | 20 |
| Na Deoxycholate | 0.5 |
| Glycerine | 24 |
| Methyl paraben | 1.8 |
| Propyl paraben | 0.2 |
| Water | q.s. | and a composition of Example 2 as follows:

| Component | Weight (mg) |
|---|---|
| Compound of Formula 1 | 60 |
| Diglyceride/Monoglyceride (8:2) | 200 |
| Propylene Glycol | 100 |
| Lecithin | 20 |
| Na Deoxycholate | 0.5 |
| Glycerine | 2.4 |
| Methyl paraben | 1.8 |
| Propyl paraben | 0.2 |
| Water | q.s. | wherein the compound of Formula 1 is:

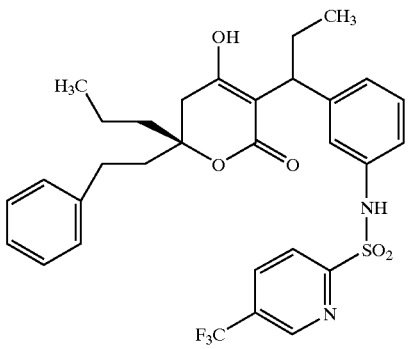

2. A submicron liquid emulsion pharmaceutical composition selected from the group consisting of a composition of Example 3 as follows:

| Component | Weight (mg) |
|---|---|
| Compound of Formula 1 | 60 |
| Diglyceride | 200 |
| Propylene Glycol | 100 |
| Lecithin | 20 |
| Na Deoxycholate | 0.5 |
| Glycerine | 24 |
| Methyl paraben | 1.8 |
| Propyl paraben | 0.2 |
| Water | q.s. | and a composition of Example 5 as follows:

| Component | Weight (mg) |
|---|---|
| Compound of Formula 1 | 60 |
| Triglyceride/Diglyceride (8:2) | 200 |
| Lecithin | 20 |
| BHT | 0.1 |
| Glycerine | 2.4 |
| Water | q.s. |

Wherein the compound of Formula 1 is:

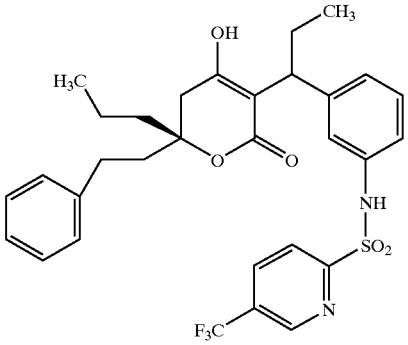

* * * * *